(12) United States Patent
Snape et al.

(10) Patent No.: US 10,695,321 B2
(45) Date of Patent: Jun. 30, 2020

(54) USE OF GLYCOPYRROLATE FOR TREATING TACHYCARDIA

(71) Applicant: Heptares Therapeutics Limited, Cambridge, Cambridgeshire (GB)

(72) Inventors: Susan Snape, Cambridgeshire (GB); Robert Tansley, Cambridgeshire (GB)

(73) Assignee: HEPTARES THERAPEUTICS LIMITED, Cambridge (GB)

( * ) Notice: Subject to any disclaimer, the term of this patent is extended or adjusted under 35 U.S.C. 154(b) by 0 days.

(21) Appl. No.: 15/011,582

(22) Filed: Jan. 31, 2016

(65) Prior Publication Data

US 2016/0143880 A1     May 26, 2016

Related U.S. Application Data

(62) Division of application No. 14/002,466, filed as application No. PCT/GB2012/050478 on Mar. 5, 2012, now abandoned.

(30) Foreign Application Priority Data

Mar. 4, 2011 (GB) .................................. 1103770.2
Feb. 9, 2012 (GB) .................................. 1202256.2

(51) Int. Cl.
| | |
|---|---|
| *A61K 31/40* | (2006.01) |
| *A61K 31/167* | (2006.01) |
| *A61K 45/06* | (2006.01) |
| *A61K 9/00* | (2006.01) |
| *A61M 15/00* | (2006.01) |
| *A61K 31/4704* | (2006.01) |

(52) U.S. Cl.
CPC ............ *A61K 31/40* (2013.01); *A61K 9/0075* (2013.01); *A61K 31/167* (2013.01); *A61K 31/4704* (2013.01); *A61K 45/06* (2013.01); *A61K 9/0078* (2013.01); *A61M 15/009* (2013.01); *A61M 15/0028* (2013.01); *A61M 15/0045* (2013.01); *A61M 2202/064* (2013.01)

(58) Field of Classification Search
CPC .... A61K 31/40; A61K 9/0075; A61K 31/167; A61K 31/4704; A61K 45/06; A61K 9/0078; A61K 31/4707; A61M 15/0028; A61M 15/0045; A61M 15/009; A61M 2202/064

See application file for complete search history.

(56) References Cited

U.S. PATENT DOCUMENTS

| | | | |
|---|---|---|---|
| 2,956,062 A | 10/1960 | Lunsford | |
| 2002/0115681 A1 | 8/2002 | Bozung et al. | |
| 2007/0270481 A1 | 11/2007 | Goede et al. | |
| 2008/0020048 A1 * | 1/2008 | Snape | A61K 31/00 424/489 |
| 2009/0209502 A1 * | 8/2009 | Haeberlin | A61K 9/0075 514/171 |
| 2010/0055045 A1 | 3/2010 | Gerhart et al. | |

FOREIGN PATENT DOCUMENTS

| | | |
|---|---|---|
| EP | 1131059 B1 | 3/2003 |
| EP | 1689360 B1 | 11/2004 |
| WO | WO 2005/105043 A2 | 11/2005 |
| WO | WO 2005/107872 A2 | 11/2005 |
| WO | WO 2005/107873 A2 | 11/2005 |
| WO | WO 2006/079625 A2 | 8/2006 |
| WO | WO 2008/000482 A1 | 1/2008 |
| WO | WO 2008/025787 A2 | 3/2008 |
| WO | WO 2010/144628 A2 | 12/2010 |

OTHER PUBLICATIONS

Noord et al (Thorax, 2010, 1-6).*
Kerwin et al (European Respiratory Journal, 2012, 40, 1106-11114).*
Boussuges ( American Journal of Respiratory and Critical Care Medicine, 2000, 162, 670-675).*
Collier et al (British Journal of Clinical Pharmacology, 1980, 9, 273-274).*
Boussuges (Year: 2000).*
Collier (Year: 1980).*
Buch, P., et al., "Reduced lung function and risk of atrial fibrillation in The Copenhagen City Heart Study." Eur Respir J., 2003, 21: 1012-1016.
Falk, Jeremy A. et al., "Cardiac Disease in Chronic Obstructive Pulmonary Disease," Proc Am Thorac Soc, 2008, 5(4): 543-548.
Grosgogeat, Y. et al., "Physiological limits of variations in heart rate measured by the Holter method in 134 normal subjects." Arch Mal Coeur Vaiss, Mar. 1986, 79(3): Abstract.
Mirakhur, R.K., Dundee, J.W., "Comparison of the effects of atropine and glycopyrrolate on various end-organs." Journal of the Royal Society of Medicine, Oct. 1980, 73: 727-730.
Meumar, Robert W. et al., "Part 8: Adult Advanced Cardiovascular Life Support, 2010 American Heart Association Guidelines for Cardiopulmonary Resuscitation and Emergency Cardiovascular Care." Circulation, 2010, 122(suppl 3): S729-S767.
Smith, L.J., "Hypotension," Veterinary Anesthesia And Pain Management Secrets, Ed. S.A. Greene, 2002, Hanley & Belfus, Philadelphia, pp. 135-140.
Valentini, Mariaconsuelo, Parati, Gianfranco, "Variables Influencing Heart Rate." Progress in Cardiovascular Diseases, 2009, 52: 11-19.

(Continued)

*Primary Examiner* — Jeffrey S Lundgren
*Assistant Examiner* — Ibrahim D Bori
(74) *Attorney, Agent, or Firm* — Saliwanchik, Lloyd & Eisenschenk

(57) ABSTRACT

The invention relates to a novel use of the antimuscarinic agent glycopyrrolate, for example the salt glycopyrronium bromide. In particular, the invention relates to glycopyrrolate for use as a heart rate lowering agent and more particularly, but not exclusively, for use in patients suffering from respiratory conditions such as chronic obstructive pulmonary disease.

25 Claims, No Drawings

(56) References Cited

OTHER PUBLICATIONS

Accord Healthcare Limited, "Package leaflet: Information for the user: Glycopyrronium Bromide 200 micrograms/ml injection (Glycopyrronium Bromide)." Sep. 2016, Sage House, 319 Pinner Road, North Harrow, Middlesex HA1 4HF, United Kingdom.
Al-Tabakha, M.M., "HPMC Capsules: Current Status and Future Prospects." J Pharm Pharmaceut Sci, 2010, 13(3): 428-442.
Ali-Melkkilä, T., et al., "Effects of glycopyrrolate and atropine on heart rate variability." Acta Anaesthesiol Scand, 1991, 35: 436-441.
Andersson, K.E., et al., "Treating patients with overactive bladder syndrome with antimuscarinics: heart rate considerations." BJU international, 2007, 100(5): 1007-1014.
Aulton, M.E., "Pharmaceutics: The Science of Dosage Form Design." Second Edition, Churchill Livingston, London, 2002, Chapters 1 and 31, pp. 9-12 and 473-488.
Bartels, C., "Determination of the pharmacokinetics of glycopyrronium in the lung using a population pharmacokinetic modelling approach" British Journal of Clinical Pharmacology, 2013, 76(6): 868-879.
Bibas, L., et al., "Diagnosis and management of supraventricular tachycardias." CMAJ, Dec. 2016, 188(17-18): E466-E473.
Hanrahan, J.P., et al., "Arrhythmias in Patient With Chronic Obstructive Pulmonary Disease (COPD): Occurrence Frequency and the Effect of Treatment With the Inhaled Long-Acting Beta2-Agonists Arformoterol and Salmeterol." Medicine, Nov. 2008, 87(6): 319-328.
Kowey, P.R., "Pharmacological Effects of Antiarrhythmic Drugs." Arch Intern Med., 1998, 158: 325-332.
Martindale Pharmaceuticals Limited, "Package leaflet: information for the user: Glycopyrronium Bromide 200 micrograms/ml Solution for Injection." Feb. 2018, Bampton Road, Harold Hill, Romform, Essex, RM3 8UG, United Kingdom.
Mercurypharma Ltd., "Package leaflet: Information for the user: Glycopyrronium Bromide 200micrograms/ml Solution for Injection." Aug. 2016, 4045, Kingswood Road, City West Business Park, Co Dublin, Ireland.
Naline, E., et al., "Effect of indacaterol, a novel long-acting β2-agonist, on isolated human bronchi." Eur Respir J, 2007, 29: 575-581.
Rosen, K.M., "Junctional Tachycardia: Mechanisms, Diagnosis, Differential Diagnosis, and Management." Circulation, 1973, 47(3): 654-664.
Collier, J.G. et al., "Salbutamol Aerosol Causes a Tachycardia Due to the Inhaled Rather than the Swallowed Fraction," *British Journal of Clinical Phamacology*, 1980, 9:273-274.
Johnson, Bruce E. et al., "Effect of Inhaled Glycopyrrolate and Atropine in Asthma," *CHEST*, 1984, 85(3):325-328.
"Anticholinergic Drugs," Study Notes, accessed from http://www.Id99.com/reference/notes/text/Anticholinergic_drugs.html, pp. 1-10, revised on Mar. 18, 2007.
Van De Maele, Boudewijn et al. "Cardiovascular Safety of QVA149, a Combination of Indacaterol and NVA237, in COPD Patients," *Journal of Chronic Obstructive Pulmonary Disease*, R2 2010, 7(6):418-427.
Tzelepis, G. et al., "Comparison of nebulized glycopyrrolate and metaproterenol in chronic obstructive pulmonary disease," *Eur Respir J.*, 1996, 9:100-103.

* cited by examiner

USE OF GLYCOPYRROLATE FOR TREATING TACHYCARDIA

CROSS REFERENCE TO A RELATED APPLICATION

This application is a divisional application of co-pending application Ser. No. 14/002,466, filed Nov. 6, 2013; which is a National Stage Application of International Application Number PCT/GB2012/050478, filed Mar. 5, 2012; which claims priority to Great Britain Applications No. 1103770.2, filed Mar. 4, 2011 and 1202256.2, filed Feb. 9, 2012; all of which are incorporated herein by reference in their entirety.

FIELD OF THE INVENTION

The invention relates to a novel use of the antimuscarinic agent glycopyrrolate, for example the salt glycopyrronium bromide. In particular, the invention relates to glycopyrrolate for use as a heart rate lowering agent and more particularly, but not exclusively, for use in patients suffering from respiratory conditions such as chronic obstructive pulmonary disease.

BACKGROUND OF THE INVENTION

Tachycardia is a type of arrhythmia which presents with a high heart rate, typically above 100 for an adult. The disorder results in a speeding of normal heart rhythm which is known as sinus tachycardia and which may be brought about by a number of factors, such as exercise, anaemia, fever, anxiety, pregnancy or drugs. Alternatively, sinus tachycardia may be caused by an underlying pathological condition as a result of an arrhythmia.

An electrocardiogram (ECG) is typically used to classify the type of arrhythmia. Tachycardias may be classified as either narrow complex tachycardias (supraventricular tachycardias) or wide complex tachycardias. Narrow and wide refer to the width of the QRS complex on the electrocardiogram (ECG). Narrow complex tachycardias tend to originate in the atria, while wide complex tachycardias tend to originate in the ventricles. Tachycardias can be further classified as either regular or irregular.

Ventricular tachycardia (VT or V-tach) is a potentially life-threatening cardiac arrhythmia that originates in the ventricles. It is usually a regular, wide complex tachycardia with a rate between 120 and 250 beats per minute. Ventricular tachycardia has the potential of degrading to the more serious ventricular fibrillation. Ventricular tachycardia is a common, and lethal, complication of a myocardial infarction (heart attack).

Supraventricular tachycardia is a type of tachycardia that originates from above the ventricles.

Examples of narrow complex tachyarrhythmias include: atrial fibrillation, atrial flutter, AV nodal reentrant tachycardia, accessory pathway mediated tachycardia, atrial tachycardia, multifocal atrial tachycardia and junctional tachycardia.

Atrial fibrillation is one of the most common cardiac arrhythmias. It is generally an irregular, narrow complex rhythm. However, it may show wide QRS complexes on the ECG if bundle branch block is present. It may be difficult to determine the rhythm's regularity when the rate exceeds 150 beats per minute. Depending on the patient's health and other variables such as medications taken for rate control, atrial fibrillation may cause heart rates that span from 50 to 200 beats per minute (or even higher if an accessory pathway is present). However, new onset atrial fibrillation tends to present with rates between 100 and 150 beats per minute.

AV nodal reentrant tachycardia (AVNRT) is the most common reentrant tachycardia. It is a regular narrow complex tachycardia that usually responds well to the Valsalva manoeuvre or the drug adenosine.

AV reentrant tachycardia (AVRT) requires an accessory pathway for its maintenance. AVRT may involve orthodromic conduction (where the impulse travels down the AV node to the ventricles and back up to the atria through the accessory pathway) or antidromic conduction (which the impulse travels down the accessory pathway and back up to the atria through the AV node).

Orthodromic conduction usually results in a narrow complex tachycardia, and antidromic conduction usually results in a wide complex tachycardia that often mimics ventricular tachycardia.

Junctional tachycardia is an automatic tachycardia originating in the AV junction. It tends to be a regular, narrow complex tachycardia and may be a sign of digitalis toxicity.

Tachycardias resulting from a fast heart rate tend either to be sinus tachycardia or an abnormal tachyarrhythmia, such as one which is supraventricular or ventriculuar in origin. The primary symptoms of sinus tachycardia may be perceived as palpitation. In susceptible individuals, this sensation can even induce anxiety. Typically, the symptoms of sinus tachycardia tend to be benign unless the patient has coexistent pathology which is worsened by a high heart rate, e.g. coronary ischaemia (angina), heart failure or heart valve disease. This can then lead to breathlessness or chest pain or in rare circumstances myocardial infarction, or acute on chronic heart failure. Tachyarrythmias may cause dizziness, fainting and black outs etc.

There is therefore a need for effective heart rate lowering agents for use in the treatment of tachycardia disorders.

SUMMARY OF THE INVENTION

According to one aspect of the invention, there is provided a pharmaceutical composition comprising glycopyrrolate or a pharmaceutically acceptable salt thereof for use as a heart rate lowering agent.

According to a further aspect of the invention, there is provided an inhalable pharmaceutical composition comprising glycopyrrolate or a pharmaceutically acceptable salt thereof for use as a heart rate lowering agent.

According to a further aspect of the invention, there is provided an inhalable unit dose comprising the pharmaceutical composition as defined herein for use in the treatment or prophylaxis of tachycardia.

According to a further aspect of the invention, there is provided an inhalation delivery device comprising one or more unit doses as defined herein for use in the treatment or prophylaxis of tachycardia.

DETAILED DESCRIPTION OF THE INVENTION

According to one aspect of the invention, there is provided a pharmaceutical composition comprising glycopyrrolate or a pharmaceutically acceptable salt thereof for use as a heart rate lowering agent.

Glycopyrrolate is an antimuscarinic agent which is useful in the treatment of conditions such as chronic obstructive pulmonary disease (COPD), asthma, cystic fibrosis (CF) and related airway diseases. It is known to provide glycopyrrolate formulations in the form of dry powder formulations, for administration using dry powder inhalers. Frequently salts of glycopyrrolate are used, such as glycopyrronium bromide.

The term "glycopyrrolate" as used in connection with the invention is intended to encompass salt forms or counterion formulations of glycopyrrolate, such as glycopyrrolate bromide, as well as isolated stereoisomers and mixtures of stereoisomers. Derivatives of glycopyrrolate are also encompassed.

It is well known that muscarinic antagonists such as glycopyrronium bromide increase the heart rate within the normal range and cause tachycardia (for example, see Markos and Snow (2006) Acta Physiol (Oxf). 186(3), 179-84 inter alia). In addition, the British National Formulary (BNF) indicates that transient bradycardia (followed by tachycardia, palpitation and arrhythmias) are one of the side-effects of antimuscarinics (BNF 62, Sep. 2011, section 1.2). Muscarinic antagonists can also induce pathological tachyarrythmias either de novo or, more commonly, in patients with a propensity for tachyarrythmias.

Furthermore, such is the pronounced role of muscarinic antagonists in causing tachycardic conditions, that one of the key indications for glycopyrronium bromide is for intra-operative bradycardia (i.e. treatment of a slow heart rate) (see BNF 62, Sep. 2011, section 15.1.3). Therefore, surprisingly, and in contradistinction with the teaching of the prior art and accepted medical literature, the inventors have identified that glycopyrronium bromide is capable of lowering the heart rate as is demonstrated in the data provided herein.

According to a further aspect of the invention, there is provided an inhalable pharmaceutical composition comprising glycopyrrolate or a pharmaceutically acceptable salt thereof for use as a heart rate lowering agent.

Data are provided herein which surprisingly demonstrates that glycopyrronium bromide administered by inhalation caused a reduction in heart rate unlike other muscarinic antagonists which are known to increase heart rate and cause conditions such as tachycardia. Furthermore, although glycopyrronium bromide has already been disclosed for the prevention of intra-operative bradycardia (i.e. increase of a slow heart-rate) the medicament is typically delivered by the intravenous route (see BNF 62, Sep. 2011, section 15.1.3). Therefore, not only is the medicament of the invention being applied for a different use to that described in the literature, but the medicament is also being delivered by an alternative route. Without being bound by theory, it is believed that inhalation of the glycopyrronium bromide has the potential to result in the heart rate lowering properties observed in the data shown herein.

In one embodiment, the composition is used in the treatment of a condition or disorder characterised by an increased heart rate and where it would be preferable to reduce the heart rate, such as tachycardia and preferably by inhalation.

It will be appreciated that the invention finds particular utility in the treatment of a condition or disorder where it would be preferable to reduce the heart rate. In addition, the invention also finds particular utility in the prevention of an increase in heart rate. Thus, in one embodiment, the composition is used as an agent for preventing an increase in heart rate. Thus, according to a further aspect of the invention, there is provided an inhalable pharmaceutical composition comprising glycopyrrolate or a pharmaceutically acceptable salt thereof for use as a heart rate suppression agent (for example, under resting conditions) as compared with intravenous glycopyrrolate administration or as compared with placebo. In one embodiment, the use is in a patient suffering from a respiratory condition, such as a condition selected from: chronic obstructive pulmonary disease (COPD), asthma, cystic fibrosis (CF) and related airway diseases. In one embodiment, the heart rate remains suppressed over a period of at least 0.75 hours, at least 1.5 hours, at least 5 hours, at least 10 hours, at least 20 hours or at least 30 hours. In one embodiment, the heart rate remains suppressed over a period of from 0.75 hours to 30 hours, from 1.5 hours to 30 hours, from 5 hours to 30 hours, from 10 hours to 30 hours, from 20 hours to 30 hours.

The glycopyrrolate may be a salt, isomer or derivative of glycopyrrolate, or mixtures thereof. In one embodiment, the glycopyrrolate is not R,R-glycopyrrolate.

In one embodiment, the glycopyrrolate or a pharmaceutically acceptable salt thereof comprises glycopyrronium bromide.

Glycopyrronium bromide (known as NVA-237) is a long-acting muscarinic antagonist is due to be launched in 2012.

It will be appreciated that the invention finds particular utility for the treatment of patients suffering from respiratory conditions such as chronic obstructive pulmonary disease (COPD), asthma, cystic fibrosis (CF) and related airway diseases who have been identified as having a risk of, or being diagnosed with, cardiac disorders which are likely to be worsened by an arrhythmia characterised by a high heart rate, i.e. tachycardia.

Tachycardia refers to a faster than normal resting heart rate where the heart rate of a resting or sleeping individual is faster than it should be. In humans, the threshold of a normal heart rate (pulse) is generally based on the person's age. Tachycardia can be dangerous depending on how hard the heart has to work. In general, the adult resting heart beats between 60 and 100 times per minute (some doctors place the healthy limit at 90). When an individual has tachyarrythmia the upper or lower chambers of the heart beat significantly faster—sometimes this happens to both chambers. When the heart beats too rapidly, it pumps less efficiently and blood flow to the rest of the body, including the heart itself is reduced. The higher-than-normal heartbeat means there is an increase in demand for oxygen by the myocardium (heart muscle)—if this persists it can lead to myocardial infarction (heart attack), caused by the dying off of oxygen-starved myocardial cells. Some patients with tachycardia may have no symptoms or complications. Tachyarrythmias in general can be associated with an increased risk of stroke, sudden cardiac arrest or death.

Mortality in COPD is more often due to cardiac rather than respiratory causes (Chhabra and Gupta (2010) Indian J Chest Dis Allied Sci 52, 225-238). The coexistence of coronary artery disease and COPD is frequent (33.6%; Falk et al (2008) Proc Am Thorac Soc 5(4), 543-548) but remains under-diagnosed. Both conditions share several similarities including the age of the population affected, a common risk factor in smoking and symptoms of exertional dyspnoea. Both the conditions are punctuated by episodes of acute exacerbations of symptoms from time to time where differentiation between these two can be especially challenging. Although coexistence of the two is common, more often, only one of the two is diagnosed resulting in under-treatment and unsatisfactory response. More specifically, tachycardia is a common symptom with patients suffering from COPD and palpitation is a characteristic symptom of tachycardia in COPD patients.

It is believed that patients with COPD tend to be prone to arrhythmia because of hypoxia, associated infections, pulmonary hypertension and structural changes to the heart, right ventricular dilatation and/or atrial dilatation.

The incidence of different arrhythmias and associated mortality varies widely in reported studies of patients with COPD, as shown in the following studies of patients with stable disease and acute exacerbations.

One study monitored 24 patients with severe COPD using continuous electrocardiographic recording (Kleiger, RE, Senior, RM. Chest 1974; 65:483). Arrhythmias were found in 84 percent of stable ambulatory patients: 72 percent of patients had arrhythmias of ventricular origin, while 52 percent had arrhythmias of supraventricular origin. A separate but related study noted that a reduced FEV1 (a marker of airway obstruction) is an independent predictor of new onset atrial fibrillation in patients with stable COPD (Buch, P, Friberg, J, Scharling, H, et al. Eur Respir 3 2003; 21:1012).

Similar results were noted in another report of 69 hypoxic patients with severe but stable COPD (Shih, HT, Webb, CR, Conway, WA, et al. Chest 1988; 94:44). Supraventricular tachycardia occurred in 69 percent, while atrial fibrillation was the basic rhythm in 8 percent. Premature ventricular beats (primarily multiform) and nonsustained ventricular tachycardia were present in 83 percent and 22 percent of patients, respectively. Both leg edema and hypercapnia, which are frequently present with cor pulmonale complicating severe COPD, were associated with an increased risk of ventricular arrhythmia. However, the presence of an arrhythmia was not associated with increased mortality.

The third study evaluated 590 patients with an acute COPD exacerbation (Fuso, L, Incalzi, RA, Pistelli, R, et al. Am 3 Med 1995; 98:272). Atrial fibrillation and ventricular arrhythmia were independent predictors of death (in addition to age and a wide alveolar-arterial oxygen gradient).

A further study evaluated 70 patients with severe COPD admitted for acute respiratory failure (Hudson, LD, Kurt, TL, Petty, TL, Genton, E. Chest 1973; 63:661). Forty-seven percent of patients had both major supraventricular and ventricular arrhythmias. In patients with acute respiratory failure, the presence of arrhythmia may be associated with increased mortality since no patient with ventricular arrhythmia survived beyond the study period.

In a large cohort of 1429 patients with COPD who underwent 5226 Holter recordings, up to 40 percent of patients had atrial tachycardias without ongoing treatment with long-acting beta agonists (Hanrahan, J P, Grogan, D R, Baumgartner, R A, et al. Medicine (Baltimore) 2008; 87:319).

More critically, studies have shown that resting tachycardia is a key factor found to decrease survival (Burrows B, Earle RH. Prediction of survival in patients with chronic airway obstruction. Am Rev Respir Dis. 1969;99:865-71).

Therefore, in one embodiment glycopyrrolate is used as a heart rate lowering agent in a patient suffering from a respiratory condition. In a further embodiment, glycopyrrolate is used as a heart rate lowering agent in a patient suffering from a condition selected from: chronic obstructive pulmonary disease (COPD), asthma, cystic fibrosis (CF) and related airway diseases. In a yet further embodiment, the glycopyrrolate is used as a heart rate lowering agent in a patient suffering from chronic obstructive pulmonary disease (COPD). Thus, according to a further aspect of the invention there is provided an inhalable pharmaceutical composition comprising glycopyrrolate for use as a heart rate lowering agent in a patient suffering from a respiratory condition, such as a condition selected from: chronic obstructive pulmonary disease (COPD), asthma, cystic fibrosis (CF) and related airway diseases, in particular chronic obstructive pulmonary disease.

It can be observed from the data presented herein that the heart rate lowering effects were demonstrated in COPD patients having resting heart rates averaging approximately 70 bpm. Therefore, the invention finds particular utility in reducing the likelihood of COPD patients developing any of the cardiac disorders mentioned hereinbefore which may increase mortality rates, such as coronary ischaemia (angina), heart failure or heart valve disease. Thus, in one embodiment, the pharmaceutical composition is used in the treatment or prophylaxis of tachycardia.

It will also be appreciated that the heart rate lowering compositions of the invention may be administered to a COPD patient already experiencing the cardiac effects mentioned hereinbefore. Thus, in an alternative embodiment, the patient has a resting heart rate of greater than 90 bpm, such as a resting heart rate of greater than 100 bpm, in particular greater than 110 bpm, e.g. greater than 120 bpm.

In one embodiment, glycopyrrolate is present within the composition in an amount of greater than 1 µg, such as between 10 and 500 µg. When the composition is delivered by the inhaled route, it will be appreciated that the amounts referred to herein refer to the amount of medicament within the composition as opposed to the amount actually delivered to the lungs of a patient. In a further embodiment, glycopyrrolate is present within the composition in an amount of between 20 and 400 µg. In a yet further embodiment, glycopyrrolate is present within the composition in an amount of between 50 and 150 µg, such as 50 µg or 100 µg. Data are presented herein (in Table 3 particularly) which shows that the most significant difference in lowering of heart rate was observed at the dosage amount of 400 µg, an effect which was reduced at the 30 hour time point. Therefore, in a further embodiment, glycopyrrolate is present within the composition in an amount of 400 µg. By contrast, the data presented herein (in Table 3 particularly) show that the dosage amount of 20 µg provided a more sustained lowering of heart rate over the entire course of the study (i.e. 30 hours). For example, −3.4 bpm at 10 hours, −3.6 bpm at 20 hours and −2.7 bpm at 30 hours. Therefore, in a further embodiment, glycopyrrolate is present within the composition in an amount of 20 µg.

In one embodiment, the pharmaceutical composition of the invention is administered once daily. It can be seen from the data presented herein (in Table 3 particularly) that the mean change in heart rate from pre-dose to 20 hours (for all doses) and pre-dose to 30 hours (for all doses other than 125 µg and 250 µg) was significantly higher than placebo. These observations confirmed that the inhaled glycopyrrolate provides a bradycardic effect which is sustained over approximately 1 to 1.5 days. Certain observations have been published which link glycopyrrolate with a slowing of the heart rate which indicates that when administered intravenously, glycopyrrolate can cause a paradoxical transient slowing of heart rate before producing tachycardic effects by countering the bradycardic effects of other agents. However, the data provided herein confirm more than a mere "transient" bradycardic effect (because the bradycardic effect was observed for as much as 30 hours) and, unlike intravenous administration, the subsequent tachycardic effect is not evident in any of the inhaled doses.

In one embodiment, the pharmaceutical composition comprises one or more pharmaceutically acceptable excipients.

It will be appreciated that glycopyrrolate is typically administered for the treatment of chronic obstructive pulmonary disease in the form of a dry powder formulation.

When the composition of the invention is formulated as a dry powder formulation, in one embodiment the composition additionally comprises a force control agent.

A force control agent is an agent which reduces the cohesion between the fine particles within the powder formulation, thereby promoting deagglomeration upon dispensing of the powder from the dry powder inhaler.

Suitable force control agents are disclosed in WO 96/23485 and WO 2005/105043 and they typically consist of physiologically acceptable material, despite the fact that the material may not always reach the lung.

The force control agent may comprise or consist of one or more compounds selected from amino acids and derivatives thereof, and peptides and derivatives thereof, the peptides suitably having a molecular weight from 0.25 to 1000 kDa.

Amino acids, peptides and derivatives of peptides are physiologically acceptable and give acceptable release or deagglomeration of the particles of active material on inhalation. Where the force control agent comprises an amino acid, it may be one or more of any of the following amino acids: leucine, isoleucine, lysine, valine, methionine, and phenylalanine. The force control agent may be a salt or a derivative of an amino acid, for example aspartame or acesulfame K. The D—and DL—forms of amino acids may also be used.

The force control agents may include one or more water soluble substances. This helps absorption of the force control agent by the body if it reaches the lower lung.

The force control agent may include dipolar ions, which may be zwitterions. It is also advantageous to include a spreading agent as a force control agent, to assist with the dispersal of the composition in the lungs. Suitable spreading agents include surfactants such as known lung surfactants (e.g. ALEC, Registered Trade Mark) which comprise phospholipids, for example, mixtures of DPPC (dipalmitoyl phosphatidylcholine) and PG (phosphatidylglycerol). Other suitable surfactants include, for example, dipalmitoyl phosphatidylethanolamine (DPPE), dipalmitoyl phosphatidylinositol (DPPI).

The force control agent may comprise a metal stearate, or a derivative thereof, for example, sodium stearyl fumarate or sodium stearyl lactylate.

Advantageously, it comprises a metal stearate. For example, zinc stearate, magnesium stearate, calcium stearate, sodium stearate or lithium stearate. In one particular embodiment which may be mentioned, the additive material comprises or consists of magnesium stearate.

The force control agent may include or consist of one or more surface active materials, in particular materials that are surface active in the solid state, which may be water soluble or water dispersible, for example lecithin, in particular soya lecithin, or substantially water insoluble, for example solid state fatty acids such as oleic acid, lauric acid, palmitic acid, stearic acid, erucic acid, behenic acid, or derivatives (such as esters and salts) thereof such as glyceryl behenate. Specific examples of such materials are phosphatidylcholines, phosphatidylethanolamines, phosphatidylglycerols and other examples of natural and synthetic lung surfactants; lauric acid and its salts, for example, sodium lauryl sulphate, magnesium lauryl sulphate; triglycerides such as Dynsan 118 and Cutina HR; and sugar esters in general. Alternatively, the force control agent may be cholesterol.

Other possible force control agents include sodium benzoate, hydrogenated oils which are solid at room temperature, talc, titanium dioxide, aluminium dioxide, silicon dioxide and starch. Also useful as force control agents are film-forming agents, fatty acids and their derivatives, as well as lipids and lipid-like materials.

Force control agents which are particularly suitable for use in the present invention include magnesium stearate, amino acids including leucine, lysine, arginine, histidine, cysteine and their derivatives, lecithin and phospholipids. The inclusion of these force control agents is expected to improve the efficacy of the glycopyrrolate for treating respiratory disorders such as COPD, asthma or cystic fibrosis.

When the composition of the invention is formulated as a dry powder formulation, in one embodiment the composition additionally comprises a carrier. In a further embodiment, the carrier comprises lactose, such as lactose monohydrate.

In certain embodiments of the invention, the composition will comprise lactose in the absence of magnesium stearate as a force control agent. For example, in one embodiment, a suitable composition of the invention comprises glycopyrronium bromide and lactose, such as 1% (w/w) glycopyrronium bromide and 99% (w/w) lactose. In certain alternative embodiments of the invention, the composition comprises glycopyrrolate, lactose and magnesium stearate. For example, in one embodiment, a suitable composition of the invention comprises glycopyrronium bromide, lactose and magnesium stearate, such as 1.05% (w/w) glycopyrronium bromide, 98.8% (w/w) lactose and 0.15% (w/w) magnesium stearate, or 1% (w/w) glycopyrronium bromide, 98.8% (w/w) lactose and 0.2% (w/w) magnesium stearate.

When present, it is believed to be important for any force control agent to be predominantly present on the surface of glycopyrrolate particles, as well as or rather than being on the surface of the carrier particles. It has been found that a high shear blending method is advantageous to achieve this.

In addition to reducing the cohesion between the fine particles of the glycopyrrolate formulation, additive materials, including the force control agents mentioned above, may have further benefits when used in the invention. It has been suggested that some force control agents, such as magnesium stearate, are able to themselves reduce the ingress of moisture into the dry powder formulation.

Furthermore, many force control agents act as surfactants. When these agents are administered to the lung, they tend to rapidly spread over the surface of the lung. It is postulated that this rapid dispersion of the surfactants may well assist in the dispersion of the glycopyrrolate in the formulation, thereby assisting and enhancing its therapeutic effect.

From the foregoing it can be seen that the desired improvements in the fine particle fraction of dry powder formulations containing glycopyrrolate for a period suitable for an inhalation product (e.g. 1, 2, 3 years) can be achieved by suitable conditioning, and/or by protection of the formulation from moisture, and/or by the suitable incorporation of an additive, such as a force control agent.

A very important advantage of the process for preparing stable formulations containing glycopyrrolate is that it allows the administration of smaller doses than previously used. The reduction of the dose is made possible by the more consistent and predictable administration of the glycopyrrolate, for example, through a consistently improved fine particle fraction and fine particle dose compared to that observed in connection with the conventional formulations. Consequently, while the dose dispensed is smaller, the amount of active agent being administered is the same, with the same therapeutic effect being achieved.

The formulations of the present invention may include glycopyrrolate as the only pharmaceutically active agent. Alternatively, the formulations may include one or more further active agents, in addition to the glycopyrrolate. The additional active agents may include, for example:

1) steroid drugs such as, for example, alcometasone, beclomethasone, beclomethasone dipropionate, betamethasone, budesonide, clobetasol, deflazacort, diflucortolone, desoxymethasone, dexamethasone, fludrocortisone, flunisolide, fluocinolone, fluometholone, fluticasone, fluticasone proprionate, fluticasone furoate, mometasone furoate, hydrocortisone, triamcinolone, nandrolone decanoate, neomycin sulphate, rimexolone, methylprednisolone and prednisolone;

2) antibiotic and antibacterial agents such as, for example, metronidazole, sulphadiazine, triclosan, neomycin, amoxicillin, amphotericin, clindamycin, aclarubicin, dactinomycin, nystatin, mupirocin and chlorhexidine;

3) systemically active drugs such as, for example, isosorbide dinitrate, isosorbide mononitrate, apomorphine and nicotine;

4) antihistamines such as, for example, azelastine, chlorpheniramine, astemizole, cetitizine, cinnarizine, desloratadine, loratadine, hydroxyzine, diphenhydramine, fexofenadine, ketotifen, promethazine, trimeprazine and terfenadine;

5) anti-inflammatory agents such as, for example, piroxicam, benzydamine, diclofenac sodium, ketoprofen, ibuprofen, heparinoid, nedocromil, sodium cromoglycate, fasafungine and iodoxamide;

6) antimuscarinic/anticholinergic agents such as, for example, atropine, benzatropine, biperiden, cyclopentolate, oxybutinin, orphenadrine hydrochloride, procyclidine, propantheline, propiverine, tiotropium, tropicamide, trospium, ipratropium bromide, GSK573719 and oxitroprium bromide;

7) anti-emetics such as, for example, bestahistine, dolasetron, nabilone, prochlorperazine, ondansetron, trifluoperazine, tropisetron, domperidone, hyoscine, cinnarizine, metoclopramide, cyclizine, dimenhydrinate and promethazine;

8) hormonal drugs such as, for example, protirelin, thyroxine, salcotonin, somatropin, tetracosactide, vasopressin or desmopressin;

9) bronchodilators, such as salbutamol, fenoterol, formoterol, indacaterol, vilanterol and salmeterol;

10) sympathomimetic drugs, such as adrenaline, noradrenaline, dexamfetamine, dipirefin, dobutamine, dopexamine, phenylephrine, isoprenaline, dopamine, pseudoephedrine, tramazoline and xylometazoline;

11) anti-fungal drugs such as, for example, amphotericin, caspofungin, clotrimazole, econazole nitrate, fluconazole, ketoconazole, nystatin, itraconazole, terbinafine, voriconazole and miconazole;

12) local anaesthetics such as, for example, amethocaine, bupivacaine, hydrocortisone, methylprednisolone, prilocaine, proxymetacaine, ropivacaine, tyrothricin, benzocaine and lignocaine;

13) opiates, such as for pain management, such as, for example, buprenorphine, dextromoramide, diamorphine, codeine phosphate, dextropropoxyphene, dihydrocodeine, papaveretum, pholcodeine, loperamide, fentanyl, methadone, morphine, oxycodone, phenazocine, pethidine and combinations thereof with an anti-emetic;

14) analgesics and drugs for treating migraine such as clonidine, codine, coproxamol, dextropropoxypene, ergotamine, sumatriptan, tramadol and non-steroidal anti-inflammatory drugs;

15) narcotic agonists and opiate antidotes such as naloxone, and pentazocine;

16) phosphodiesterase type 5 inhibitors, such as sildenafil; and 17) pharmaceutically acceptable salts of any of the foregoing.

In one embodiment, the additional active agents are pharmaceutically active agents which are known to be useful in the treatment of respiratory disorders, such as $\beta_2$-agonists, steroids, antimuscarinics/anticholinergics, phosphodiesterase 4 inhibitors, and the like. In one embodiment, the formulation of the invention does not include formoterol.

In one particular embodiment which may be mentioned, the additional active agent includes indacaterol. Indacaterol is an ultra-long-acting beta-adrenoceptor agonist currently approved in Europe as OnbrezTM, marketed by Novartis. It is licensed for the treatment of chronic obstructive pulmonary disease (COPD) and is delivered as an aerosol formulation in the BreezhalerTM dry powder inhaler. A combination product of indacaterol and glycopyrronium bromide (known as QVA-149) is currently in Phase III clinical trials for COPD and is due to be launched in 2013.

In an alternative embodiment, the additional agent includes formoterol fumarate. A dual combination product of formoterol fumarate and glycopyrrolate (known as PT003) is scheduled to enter Phase III clinical trials for COPD in 2012 and is currently being developed by Pearl Therapeutics, Inc. A triple combination product of formoterol fumarate, glycopyrrolate and an inhaled corticosteroid (known as PT010) is currently being developed by Pearl Therapeutics, Inc.

In an alternative embodiment, the additional agent includes a beta agonist, such as a $\beta_2$-agonist. It is well known that such beta agonists cause tachycardia (see The Merck Manuals Online Medical Dictionary—Chronic Obstructive Pulmonary Disease). Thus, in one embodiment, the composition of the invention is used in the concomitant treatment of a patient suffering from a respiratory condition and being treated with a beta agonist.

In a further embodiment, the pharmaceutical composition comprising glycopyrrolate or a pharmaceutically acceptable salt thereof is administered to a patient population which suffers from tachycardia which has been pharmaceutically induced.

The pharmaceutical composition comprising glycopyrrolate or a pharmaceutically acceptable salt thereof is administered to a patient in which tachycardia has been induced or exacerbated by an inhalable drug, more preferably an inhalable drug used for treating a pulmonary disorder, more preferably salbutamol. The drug may alternatively be ephedrine, amphetamines or cocaine. Preferably, the administration of the pharmaceutical composition comprising glycopyrrolate or a pharmaceutically acceptable salt thereof is separate or sequential to that of the tachycardia inducing drug. Where administration is separate or sequential, preferably administration of the glycopyrrolate or a pharmaceutically acceptable salt thereof takes place within 4 hours of the tachycardia inducing drug, preferably within 2 hours of the tachycardia inducing drug, preferably within 1 hour of the tachycardia inducing drug, preferably within 10 minutes of the tachycardia inducing drug.

In a further embodiment, the pharmaceutical composition comprising glycopyrrolate or a pharmaceutically acceptable salt thereof is administered to a patient population which suffers from tachycardia which has not been pharmaceutically induced, such as an endocrine disorders, for example pheochromocytoma or hyperthyroidism.

Preferably, the pharmaceutical composition comprising glycopyrrolate or a pharmaceutically acceptable salt thereof is administered to a patient population which suffers from a form of tachycardia selected from the group consisting of ventricular tachycardia, supraventricular tachycardia, atrial fibrillation, AV nodal reentrant tachycardia (AVNRT), AV reentrant tachycardia (AVRT) and junctional tachycardia.

It will be appreciated that the compositions of the invention may be formulated in accordance with known procedures. In particular, the skilled person is directed to the contents of WO 2005/105043 which provide a detailed description of how stable formulations containing glycopyrrolate may be prepared. In particular, formulations may be prepared which are stable for a period of at least 1 year, such as a period of at least 2 years and in particular a period of at least 3 years.

The stability of a composition should be indicated by consistent dispersability of the powder over these periods, which may, for example, be measured in terms of a consistently good fine particle fraction or fine particle dose over time. In one embodiment of the stable composition, the fine particle fraction (<5 µm) is consistently greater than about 30% over a period of at least 1 year, at least 2 years or at least 3 years when stored at normal temperatures and humidities for pharmaceutical products. In another embodiment of the invention, the fine particle fraction (<5 µm) is consistently greater than about 40% over a period of at least 1 year, at least 2 years or at least 3 years. In one embodiment, the fine particle fraction (<5 µm) is consistently greater than 30% or greater than 40% when the formulations are stored under standard testing conditions, such as 25° C./60% RH, 30° C./60% RH, 40° C./70% RH or 40° C./75% RH.

In one embodiment of the stable composition, the fine particle fraction of the dry powder formulations is consistently at least about 30%, at least about 40%, at least about 50%, at least about 60%, at least about 70% or at least about 80%.

In one embodiment of the stable composition, the fine particle dose of the dry powder formulations is consistently at least about 30%, at least about 40%, at least about 50%, at least about 60%, at least about 70% or at least about 80%.

In another embodiment of the stable composition, the dry powder formulations are packaged for storage and/or delivery by a dry powder inhaler and the packaged formulations are stable for at least 1, 2 or 3 years when stored at normal temperatures and humidities, i. e. the packaged formulations or products comprising the formulations do not have to be stored in a controlled environment in order to exhibit the desired stability.

As the instability of the conventional glycopyrrolate formulations appears to be due to moisture absorption, there are a number of measures which are proposed to increase stability.

Firstly, the amorphous content of the glycopyrrolate is to be reduced by improving the processing of the glycopyrrolate. Where the glycopyrrolate is micronised, the micronisation process may be improved, for example, by adjusting the conditions under which the milling takes place, to prevent the formation of amorphous material. Additionally or alternatively, the micronised product may be "conditioned" to remove the amorphous material.

Alternatively, the particles of glycopyrrolate may be engineered so that they include little or no amorphous material. Suitable methods for doing this are known to those skilled in the art. For example, glycopyrrolate powders with low non-crystalline content may be made using methods such as supercritical fluid processing using carbon dioxide, or other controlled forms of crystallisation or precipitation, such as slow precipitation, by emulsion methods, sono-crystallisation and the like.

Secondly, the exposure of the dry powder formulation to moisture when the powder is stored is suitably reduced. In this regard, it is particularly desirable to reduce exposure of the formulation to moisture during storage in capsules or blisters.

Finally, the inclusion of additive materials in the dry powder formulation can enhance the powder dispersability and protect the formulation from the ingress of moisture.

Batches of micronised glycopyrrolate were obtained and, following sealed storage for several weeks, the physical changes of the material from fine cohesive powders to solid agglomerates were observed.

The following section summarises the tests conducted on reported batches of glycopyrrolate received following micronisation:

Batch A:
Micronised at 0.5 kg/hr
Injection pressure: 10 bar
Micronisation pressure: 7 bar
Sympatec sizing: d10 0.7 µm, d50 1.8 µm, d90 3.6 µm
Loss on drying: 0.7%
DVS indicated crystalline material. On storage, soft lumps of material were found in bulk powder, and repeated particle sizing gave d50 values ranging between 2.6 and 3.5 µm.

Batch B:
Micronised at 0.5 kg/hr
Injection pressure: 10 bar
Micronisation pressure: 7 bar
Sympatec sizing: d10 1.0pm, d50 2.4 µm, d90 4.8 µm
Loss on drying: 0.6%
Water activity: 54% RH
DVS indicated amorphous material was present. On storage, large hard lumps of material were found, and repeated particle sizing gave d50 values ranging between 36 and 160 µm.

Batch C:
Micronised at 0.4 kg/hr
Injection pressure: 10 bar
Micronisation pressure: 9.8 bar
Sympatec sizing: d10 0.8 µm, d50 2.3 µm, d90 4.8 µm
Loss on drying: 0.4%
DVS indicated amorphous material was present. On storage, large hard lumps of material were found in bulk powder, and repeated particle sizing gave d50 value of 51 µm.

Remicronised Batch C:
Micronised at 0.5 kg/hr
Injection pressure: 10 bar
Micronisation pressure: 9 bar
Sympatec sizing: d10 1.0 µm, d50 2.4 µm, d90 4.5 µm
Loss on drying: 0.5%
On storage, only soft lumps of material were found in bulk powder.

This summary shows that selected batches of micronised glycopyrrolate had formed hard agglomerates, and this appears to be associated with the presence of amorphous material, as the first batch, which contained no detectable amorphous material, exhibited good powder properties following storage. Consequently, it is believed that the formation of hard agglomerates occurs within a micronised powder that contains surface non-crystalline material, whether formulated with excipient, any moisture protection agent, a force control agent, or on its own.

The amorphous material will be located on the surface to have the greatest effect of this kind. The quantity of amorphous material relative to the bulk mass may be very small, as long as it is sufficient to produce this effect. The non-crystalline material will draw moisture from its surroundings. Sources of moisture may include the surrounding air or gas, the surrounding excipients or additives (such as lactose or force control agents), the packaging or device, such as a gelatin or other capsule material, or a plastic.

Tests have shown that all micronised glycopyrronium bromide prototype formulations made using conventional methods, including those that comprise additives (including magnesium stearate), have been found to degrade or deteriorate in aerosolisation performance over a period of 6 months. This deterioration has even been found to occur when stored under dry conditions. Deterioration in performance has been seen to be approximately 30 to 50% of original performance or more. Such deterioration would make these formulations unattractive for commercial use.

It has been suggested that conducting micronisation under the use of humidified air or other gas may help to reduce the generation of amorphous materials. Both WO 99/54048 and WO 00/32165 disclose that milling under increased humidity can reduce the generation of amorphous material. WO 00/32313 discloses the milling of material at reduced temperature using helium or a mixture of helium and another gas in order to reduce the formation of amorphous material. It should be noted that none of these prior art documents disclose that the milling of glycopyrrolate under these special conditions is beneficial.

However, the milling conditions disclosed in the prior art are not standard in micronisation practice and it may well prove to be difficult to control these processes. It may also prove difficult to use such processes on a commercial scale.

Finally, the extent to which such processes may help to control the generation of amorphous material for the specific problem of glycopyrrolate is also not known.

As mentioned above, glycopyrrolate presents particular problems because of its inherent instability.

In accordance with one embodiment of the stable composition, the dry powder formulation comprising glycopyrrolate is prepared using a process, suitably a micronisation process, which is carried out under conditions which reduce the formation of amorphous material. Examples of suitable micronisation conditions include increased relative humidity (for example 30-70%) or micronisation using helium at reduced temperatures.

In another embodiment, the dry powder formulation comprising glycopyrrolate is micronised and then undergoes a "conditioning" step to remove or reduce the amorphous material content. Such conditioning steps include exposure to moisture to encourage re-crystallisation of the amorphous material without the formation of hard agglomerates. Examples of such conditioning are discussed in more detail below.

Examples of suitable dry powder formulations which may be used in accordance with the invention include those described in WO 2008/000482 such as Examples 1 and 2 below:

EXAMPLE 1

37 g of magnesium stearate are mixed with 1 kg of crystalline glycopyrronium bromide in a Turbula(R) blender for 5 hours. The resulting mixture is micronised using a Hosokawa Alpine(R) 100 AFG fluid bed opposed jet mill with the following parameters: classifier speed, 13000 rpm; milling gas pressure, 3.5 bar. The mill is equipped with 3 nozzles of 1.9 mm diameter.

The resulting mixture has a median particle size of about 3 micron (x90=7 micron, x50=3 micron, x10=1 micron). The magnesium stearate is well distributed over the drug substance surface.

Lactose carrier particles (99.7% w/w of final composition) are admixed to give an inhalable dry powder.

EXAMPLE 2

Drug substance 1: 50 g of magnesium stearate are mixed with 1 kg of crystalline glycopyrronium bromide in a Turbula(R) blender for 5 hours. The resulting mixture is micronised using a Hosokawa Alpine(R) 100 AFG fluid bed opposed jet mill (equipped with 3 nozzles of 1.9 mm diameter) with the following parameters: classifier speed, 13000 rpm; milling gas pressure, 3.5 bar, to give particles that have an average particle size of less than 5 microns.

Drug substance 2: 1 kg of crystalline glycopyrronium bromide is micronised using a Hosokawa Alpine(R) 100 AFG fluid bed opposed jet mill (equipped with 3 nozzles of 1.9 mm diameter) with the following parameters: classifier speed, 13000 rpm; milling gas pressure, 3.5 bar, to give particles that have an average particle size of less than 5 microns.

These drug substances are used to prepare the following formulations:

Formulation 1: Lactose carrier particles (99% w/w of final composition) are admixed with drug substance 2 to give an inhalable dry powder.

Formulation 2: Lactose carrier particles (98.8% vv/w of final composition) and magnesium stearate (0.15%) are admixed with drug substance 2 to give an inhalable dry powder.

Formulation 3: Lactose carrier particles (98.8% w/w of final composition) and magnesium stearate (0.15%) are admixed with drug substance 1 to give an inhalable dry powder.

The resulting powders are filled in aliquots of 25 mg into size 3 hydroxypropylmethyl-cellulose (HPMC) capsules. The resulting capsules are tested for aerodynamic particle size distribution (fine particle fraction) either immediately after manufacture or after storage under different conditions.

The fine particle fraction (FPF) and emitted dose (ED) of the powder in each capsule is measured using the Next Generation Impactor (NGI) particle-classifying cascade impactor at a flow rate of 85 L/min.

According to a further aspect of the invention there is provided an inhalable unit dose comprising the pharmaceutical composition as hereinbefore defined for use in the treatment or prophylaxis of tachycardia. In one embodiment, the unit dose comprises a capsule. In a further embodiment, the capsule is opaque or transparent. In a further embodiment, the capsule is transparent. Such an embodiment provides the advantage of informing a user that successful inhalation of the dosage has been achieved.

In one embodiment, the capsule comprises a gelatin capsule. It is known for gelatin capsules to contain in the order of 10 to 15% w/w water, and for this to provide a sufficient source of water to create a moisture instability problem.

The moisture content of the gelatin capsules has been shown to drop as the water is extracted by the capsule contents. The water content in the gelatin capsules acts as a plasticizer so that when the water is extracted and the water content drops, the capsules become more brittle, which will affect piercing and the like.

An article on improvements in hypromellose capsules (B. E. Jones, Drug Delivery Technology, Vol 3 No. 6, page 2, 2003), describes the problems associated with gelatin capsules for use in dry powder inhalers. These problems include changes in brittleness and hence piercing consistency, and related dispersion performance as a function of the changes in gelatin moisture content. The potential of the gelatin to act as a moisture source, which can be released to the powdered contents of the capsule, is also discussed, as are the variations in electrostatic charge properties.

In one embodiment, the capsule is made with hypromellose (HPMC) or other celluloses or cellulose derivatives which do not rely on moisture as a plasticizer. The moisture content of such capsules can be less than 10%, or even below 5% or 3% w/w, and this makes such capsules more suitable for use with glycopyrrolate.

Capsules can also be made from gelatin containing one or more plasticizers other than water, such as PEG, glycerol, sorbitol, propyleneglycol or other similar polymers and co-polymers, hence allowing the moisture content to be reduced to below 10%, or even below 5% or 3% w/w.

Alternatively, capsules can be made from synthetic plastics or thermoplastics (polyethylene or polycarbonate or related plastics) containing reduced moisture content below 10%, or even below 5% or 3% w/w. Further alternative capsules with reduced moisture content are made from starch or starch derivatives or chitosan.

In the foregoing capsules, the problem of brittleness is reduced. Furthermore, capsules such as those made from celluloses have been found to pierce more consistently and reliably, and the pierce hole made appears to be more cleanly formed and spherical, with less shedding of particles. The aerosolisation of the powder contents has also been found to be improved, as well as being more consistent.

According to a further aspect of the invention there is provided an inhalation delivery device comprising one or more doses of the pharmaceutical composition as hereinbefore defined for use in the treatment or prophylaxis of tachycardia. In one embodiment, the delivery device is an inhaler. In a further embodiment, the delivery device is a pressurised metered dose inhaler. It will be appreciated that the metered dose inhaler may suitably comprise a reservoir containing device or a multi-unit dose containing device or a unit dose containing device. It will also be appreciated that the pressurised metered dose inhaler may be suitable for when the composition of the invention additionally comprises propellants such as hydrofluoroalkanes (HFAs) and the like or any such propellant suitable for use with compositions of the invention. Examples of formulations according to the invention which are suitable for administration by pressurised metered dose inhalers (pMDIs) include those developed by Pearl Therapeutics, Inc. such as PT001 (glycopyrrolate HFA-MDI monotherapy for COPD), PT003 (combination of glycopyrrolate and formoterol fumarate HFA-MDI formulation for COPD) and PT010 (triple combination of glycopyrrolate, formoterol fumarate and an inhaled corticosteroid as an HFA-MDI formulation for COPD). A further example includes a pMDI formulation containing 100 μg glycopyrrolate which has been used in clinical trials by Chiesi Farmaceutici S.p.A.

In one embodiment, the delivery device is a nebulizer.

In a further embodiment, the delivery device is a dry powder inhaler. Examples of suitable devices include, but are not limited to, the TURBUHALER (Astra Zeneca), CLICKHALER, DUOHALER (Innovata Biomed), EASYHALER (Orion), ACCUHALER, DISKUS, DISKHALER, ROTAHALER, GEMINI (GlaxoSmithKline), HANDIHALER, INHALATOR, AEROHALER (Boehringer Ingelheim), TWISTHALER (Schering Plough), AEROLIZER, BREEZHALER, SOLIS (Novartis), MONOHALER (Miat), AIRMAX, CYCLOHALER (Teva), GENUAIR (Almirall), NEXTDPI (Chiesi) and NOVOLIZER (ASTA Medica).

In one embodiment, the inhaler device includes a means for protecting the formulation from moisture, for example within a sealed blister, such as a foil blister, with suitable sealing to prevent the ingress of moisture. Such an embodiment seeks to solve the problem of moisture absorption by dry powder glycopyrrolate formulations. Such devices are known, for example the GYROHALER (Vectura) or DISKUS (GlaxoSmithKline) devices.

It is believed to be particularly advantageous if the blister is pierced using a simple mechanism, such as with the GYROHALER. This device and this technology has been developed by Vectura and relates to an inhalation device for oral or nasal delivery of a medicament in powdered form. The powdered medicament is stored in a strip of blisters and each blister has a puncturable lid. When the inhaler is to be used, the lid of the aligned blister is punctured, thereby allowing an airflow through the blister to be generated to entrain the dose contained therein and to carry the dose out of the blister and into the user's airway via the inhaler mouthpiece. This arrangement with blisters having puncturable lids allows the blisters to have the best possible seal. In contrast, in blister systems such as the Diskus where the lids of the blisters are peeled open, it is more difficult to maintain an optimum seal due to the restrictions on the nature of the bond required to allow peeling to occur.

In a further embodiment, the dry powder formulation comprising glycopyrrolate is stored in packaging made from a material which itself has a moisture content of less than 10%, such as less than 5% and in particular less than 3%.

The packaging should also suitably prevent the ingress of moisture, so that the powder is protected from external sources of moisture. Foil sealed blisters are an example of a packaging which prevents ingress of moisture.

In this latter regard, the prevention of the ingress of moisture from external sources may be assisted by further packaging. For example, HPMC capsules may be stored in a sealed environment, such as an additional layer of foil packaging.

In an alternative embodiment, the dry powder formulation is dispensed from a multidose dry powder inhaler device wherein the powder is stored in a reservoir as opposed to individually packaged doses. In such an embodiment, the device should offer superior moisture protection compared to conventional reservoir devices. For example, the device should include one or more of the following features: a sealed reservoir chamber (for example including a sealing gasket to seal the reservoir chamber), plastics materials exhibiting very low moisture permeability (for forming the walls of the reservoir chamber), and a desiccant.

According to a further aspect of the present invention, there is provided a pharmaceutical composition as defined herein, contained in a package which further comprises instructions for administering said composition to a patient in need of a heart rate lowering agent, or in anticipation of the need of a heart rate lowering agent. Preferably, the instructions comprise directions for administering said composition to a patient suffering from tachycardia or in need of prophylaxis of tachycardia.

According to a further aspect of the present invention, there is provided an inhalable unit dose as defined herein, contained in a package which further comprises instructions for administering said composition to a patient in need of a heart rate lowering agent, or in anticipation of the need of a heart rate lowering agent. Preferably, the instructions comprise directions for administering said composition to a patient suffering from tachycardia or in need of prophylaxis of tachycardia.

According to a further aspect of the present invention, there is provided an inhalation delivery device as defined herein, contained in a package which further comprises instructions for administering said composition to a patient in need of a heart rate lowering agent, or in anticipation of the need of a heart rate lowering agent. Preferably, the instructions comprise directions for administering said composition to a patient suffering from tachycardia or in need of prophylaxis of tachycardia.

According to a further aspect of the present invention, there is provided a method of treatment or prophylaxis of a condition or disorder characterised by an increased heart rate, such as tachycardia, said method comprising administering an effective amount of an inhalable pharmaceutical composition comprising glycopyrrolate or a pharmaceutically acceptable salt thereof to a patient in need thereof. The method preferably comprises administering the composition to a patient who also suffers from a respiratory condition, such as a condition selected from: chronic obstructive pulmonary disease (COPD), asthma, cystic fibrosis (CF) and related airway diseases.

The following study illustrates the invention:

Study Methodology (a) Study Design and Plan

The study was a Phase IIa, multi-centre, randomised, double-blind, placebo-controlled, crossover, dose-ranging study using four dose levels of glycopyrronium bromide in subjects with COPD. A total of 40 subjects were required to complete the study.

Subjects were randomised to receive a single inhaled dose of 20, 125, 250 and 400 µg of glycopyrronium bromide in ascending order, with a placebo dose randomised into the sequence over 5 study visits. Subjects were randomised to receive treatment on Study Day 1 prior to dosing. All doses, including placebo, were administered using the Miat Monohaler.

The study consisted of a Screening period, Treatment period of five study visits (separated by a 5-14-day wash-out period), and a Follow-up Visit, 7-14 days after final treatment and prior to discharge from the study.

(b) Study Timing

Subjects underwent an initial pre-screening visit to sign an Informed Consent Form (ICF), followed by a Screening Visit to confirm eligibility. The Pre-screening Visit and Screening Visit could have been combined if the subject signed the ICF and had not taken any bronchodilators within the prohibited period before the pulmonary function tests (PFTs). Following the Screening Visit, subjects were then randomised on Study Day 1 prior to dosing.

The Treatment period then consisted of five study visits (separated by a 5-14-day wash-out period), during which subjects were dosed with a single inhaled dose of glycopyrronium bromide using a Miat Monohaler, in ascending order (20, 125, 250 or 400 µg). A placebo was randomly administered (using a Miat Monohaler) at one of the study visits; subsequent visits continued with the next highest dose of glycopyrronium bromide to that which was administered prior to the placebo.

At the end of the study, subjects were required to attend the clinic for a Follow-up Visit, 7-14 days after final treatment. The subjects were then discharged from the study.

Each subject was expected to be involved in the study for between 8-10 weeks.

(c) Study Population

The population to be studied were to be male or female, aged 40 years and over with a diagnosis of mild-moderate COPD that was responsive to anti-cholinergic therapy. Responsiveness to anti-cholinergic therapy is defined as an increase in $FEV_1$ of 12% and at least 150 ml following administration of 80 µg ipratropium bromide.

(i) Number of Subjects

Up to 140 subjects were to be screened and 40 subjects were required to complete the study.

The estimate of number of subjects to be screened was based on screening data from previous studies where subjects had to demonstrate reversibility in order to be eligible to participate in the study. This information indicated that between 2 and 4 subjects would need to be screened to achieve one eligible subject. The maximum number of eligible subjects to be enrolled was not specified as it was not known how many subjects were likely to prematurely discontinue from the study.

(ii) Selection Criteria

Inclusion Criteria

Subjects were included in the study providing they met the following criteria:

1. Male or female, aged 40 years or over.
2. Had been diagnosed with COPD (cough, sputum production, dyspnoea, and/or a history of exposure to risk factors for the disease).
3. Were current or ex-smokers with a smoking history of at least 10 pack years.
4. Had a pre-bronchodilator $FEV_1$ between 40% and 80% of the predicted normal value.
5. Had a pre-bronchodilator $FEV_1/FVC$ ratio of <70%.
6. Improved their $FEV_1$ by 12% or more and by at least 150 ml after administration of 80 µg Atrovent (ipratropium bromide) delivered via spacer.
7. Were willing and able to withhold long-acting anticholinergic therapy during the study.
8. Were able to understand the nature of the study and give written informed consent.

Exclusion Criteria

Subjects were excluded from the study for any of the following reasons:

1. Were pregnant or breast-feeding. Women of child bearing potential had to use an adequate method of contraception during the course of the study and had to have a negative pregnancy test prior to receiving study drug.
2. Had a history of narrow-angle glaucoma, prostatic hyperplasia or bladder neck obstruction.
3. Had significant concurrent cardiac, renal, hepatic or metabolic disease.
4. Had evidence of atopy, allergic rhinitis, or, in the investigator's opinion, had predominant asthma rather than COPD.
5. Had a blood eosinophil cell count >600 $mm^3$.
6. Had been treated with oral steroids 8 weeks prior to screening or for 4 or more weeks in the 12 months prior to Screening Visit.
7. Were receiving inhaled corticosteroids or oral theophylline, but had not maintained a stable dose in the 4 weeks prior to Screening Visit, and were not able to maintain a stable dose during the treatment period.

8. Were sensitive to antimuscarinic agents.
9. Required oxygen therapy.
10. Had experienced an upper respiratory tract infection or had exacerbations of their COPD requiring treatment with antibiotics in the 6 weeks prior to Screening Visit.
11. Had taken part in any other clinical trial involving administration of an investigational drug within the 3 months prior to the start of dosing.

(d) Study Treatment (i) Treatments Administered

All subjects were scheduled to be dosed between 08:00 and 10:00 am. For individual subjects, dosing was at the same time of day (±30 minutes). At each dosing visit, subjects received a single dose of glycopyrronium bromide or placebo administered via Miat Monohaler. Each different dose (20, 125, 250 or 400 µg) was contained in one capsule. An appropriate number of Miat Monohalers to conduct the study was also supplied to the site. A new Miat Monohaler was used to administer each dose at each visit.

On the ward, the study nurse placed each capsule into the Miat Monohaler for the subject to inhale. This was done immediately prior to the inhalation. For each capsule the subjects were asked to inhale twice through the Miat Monohaler.

(ii) Description of Investigational Product copyrronium bromide was presented in size 3, white opaque, hard, gelatin capsules packaged in aluminium pouches. The capsules were presented in four dose strengths containing 20, 125, 250, or 400 µg glycopyrronium bromide. In addition to glycopyrronium bromide, excipient present in the capsule formulation consisted of the PowderHale™ formulation of lactose and magnesium stearate.

TABLE 1

| Formulation of Investigational Product | | | | |
|---|---|---|---|---|
| | Product Description | | | |
| | 20 µg | 125 µg | 250 µg | 400 µg |
| Glycopyrronium bromide/ PowderHale ™ (% w/w) | 0.08 | 0.50 | 1.60 | 1.60 |
| Capsule fill weight (mg) | 25.0 | 25.0 | 15.6 | 25.0 |

A placebo-to-match product was also provided which consisted of size 3 white, opaque, hard gelatin capsules containing the non-active PowderHale™ formulation alone.

Glycopyrronium bromide capsules for inhalation were stored below 25° C. in a dry place.

(iii) Selection and Timing of Dose for Individual Subjects

Each subject received 20, 125, 250 and 400 µg glycopyrronium bromide in ascending order, with a placebo dose randomised into the sequence over five study visits (i.e., one dose per visit).

All subjects were scheduled to receive study medication between 08:00 am and 10:00 am. Study medication was administered to each subject at approximately the same time (within 30 minutes) on each study day.

(e) Study Assessments

All vital signs were measured on each study day, including heart rate (with the subject semi-supine for 5 minutes prior to measurement); blood pressure; respiratory rate and temperature were measured at each visit and before receiving study medication (pre-treatment), if applicable. Blood pressure and heart rate were also measured at 45, 90 minutes and 5, 10, 20 and 30 hours post-treatment on study days.

(f) Planned Statistical Analysis

The statistical analyses were to be reported using summary tables and data listings. Statistical tests for the evaluation were to be performed at the 0.05 significance level using a two-sided test.

All analyses and tabulations were to be performed using SASS Version 6.12 on a PC platform. Continuous variables were to be summarised with sample size (n), mean, standard deviation (SD), minimum, median, and maximum. The median, minimum and maximum was to be displayed to the same number of decimal places the results were to be recorded to. The mean was to have one extra decimal place and the standard deviation was to have two extra decimal places. Categorical variables were to be summarised with number and percentage of subjects.

Results

The results of this study may be seen in Tables 2-4.

All subjects had normal heart rate at the time of screening. Following the study, there was a dose dependent decrease in mean heart rate from Test Day Baseline up to 5 hours post-dose.

At 10 hours, the decrease in mean heart rate from Test Day Baseline was intermittent, with the greatest decrease recorded in the 400 µg treatment group at −6.4 bpm.

At 20 hours, the decrease in mean heart rate from Test Day Baseline was also intermittent, with the greatest decrease recorded in the 400 µg treatment group at −5.6 bpm.

Statistical significance was achieved at the 45 minute to 10 hour timepoints, inclusive, relative to placebo ($p<0.05$) for the 400 µg dose.

TABLE 2

| | Vital Signs - Heart Rate (bpm) | | | | |
|---|---|---|---|---|---|
| Time Point | 20 µg (N = 45) | 125 µg (N = 43) | 250 µg (N = 41) | 400 µg (N = 40) | Placebo (N = 42) |
| Pre-dose | | | | | |
| n | 45 | 42 | 41 | 40 | 41 |
| Mean | 72.8 | 69.3 | 70.8 | 72.7 | 70.6 |
| SD | 11.73 | 10.58 | 12.16 | 11.01 | 10.62 |
| Min | 48 | 50 | 50 | 54 | 52 |
| Median | 72.0 | 68.0 | 68.0 | 72.0 | 70.0 |
| Max | 105 | 93 | 115 | 100 | 100 |
| 45 mins post-dose | | | | | |
| n | 45 | 42 | 40 | 40 | 41 |
| Mean | 70.3 | 65.5 | 65.1 | 65.4 | 68.0 |
| SD | 11.65 | 9.94 | 9.44 | 9.09 | 9.82 |
| Min | 49 | 50 | 48 | 52 | 52 |

TABLE 2-continued

| Vital Signs - Heart Rate (bpm) | | | | | |
|---|---|---|---|---|---|
| Time Point | 20 µg (N = 45) | 125 µg (N = 43) | 250 µg (N = 41) | 400 µg (N = 40) | Placebo (N = 42) |
| Median | 68.0 | 63.5 | 64.0 | 65.0 | 67.0 |
| Max | 113 | 88 | 90 | 91 | 87 |
| 90 mins post-dose | | | | | |
| n | 45 | 42 | 39 | 40 | 41 |
| Mean | 72.5 | 67.6 | 68.2 | 67.1 | 71.6 |
| SD | 13.61 | 10.29 | 9.65 | 10.19 | 10.68 |
| Min | 51 | 47 | 51 | 50 | 50 |
| Median | 71.0 | 69.0 | 69.0 | 67.5 | 70.0 |
| Max | 126 | 87 | 92 | 89 | 98 |
| 5 hrs post-dose | | | | | |
| n | 45 | 40 | 40 | 39 | 41 |
| Mean | 72.8 | 70.6 | 68.4 | 69.7 | 72.2 |
| SD | 11.89 | 10.89 | 10.96 | 9.61 | 11.46 |
| Min | 48 | 48 | 53 | 49 | 53 |
| Median | 74.0 | 73.0 | 68.5 | 69.0 | 72.0 |
| Max | 95 | 96 | 97 | 87 | 109 |
| 10 hrs post-dose | | | | | |
| n | 43 | 39 | 39 | 38 | 39 |
| Mean | 69.1 | 67.0 | 66.3 | 65.7 | 68.5 |
| SD | 10.27 | 10.47 | 10.62 | 8.96 | 10.03 |
| Min | 50 | 48 | 49 | 49 | 49 |
| Median | 68.0 | 67.0 | 65.0 | 65.5 | 68.0 |
| Max | 88 | 90 | 97 | 84 | 97 |
| 20 hrs post-dose | | | | | |
| n | 44 | 40 | 39 | 36 | 40 |
| Mean | 68.8 | 66.4 | 66.6 | 66.7 | 68.1 |
| SD | 9.76 | 9.36 | 10.04 | 8.67 | 8.71 |
| Min | 48 | 51 | 50 | 52 | 51 |
| Median | 69.5 | 66.0 | 65.0 | 66.0 | 67.5 |
| Max | 95 | 90 | 100 | 83 | 98 |
| 30 hrs post-dose | | | | | |
| n | 43 | 38 | 38 | 36 | 39 |
| Mean | 69.8 | 72.1 | 70.7 | 70.9 | 71.1 |
| SD | 10.69 | 10.46 | 11.38 | 10.52 | 9.22 |
| Min | 42 | 55 | 47 | 42 | 42 |
| Median | 70.0 | 72.0 | 71.5 | 70.0 | 71.0 |
| Max | 93 | 103 | 95 | 96 | 100 |

TABLE 3

| Vital Signs - Heart Rate (bpm) - Change from Test day Baseline | | | | | |
|---|---|---|---|---|---|
| Time Point | 20 µg (N = 45) | 125 µg (N = 43) | 250 µg (N = 41) | 400 µg (N = 40) | Placebo (N = 42) |
| Pre-dose | | | | | |
| n | 45 | 42 | 41 | 40 | 41 |
| Mean | 72.8 | 69.3 | 70.8 | 72.7 | 70.6 |
| SD | 11.73 | 10.58 | 12.16 | 11.01 | 10.62 |
| Min | 48 | 50 | 50 | 54 | 52 |
| Median | 72.0 | 68.0 | 68.0 | 72.0 | 70.0 |
| Max | 105 | 93 | 115 | 100 | 100 |
| Change from pre-dose to 45 mins post-dose | | | | | |
| n | 45 | 42 | 40 | 40 | 41 |
| Mean | −2.5 | −3.8 | −4.6 | −7.4 | −2.7 |
| SD | 8.61 | 5.74 | 6.05 | 7.23 | 5.72 |
| Min | −16 | −17 | −20 | −22 | −15 |
| Median | −2.0 | −4.0 | −4.5 | −6.5 | −3.0 |
| Max | 37 | 10 | 10 | 4 | 11 |
| Change from pre-dose to 90 mins post-dose | | | | | |
| n | 45 | 42 | 39 | 40 | 41 |
| Mean | −0.2 | −1.8 | −1.7 | −5.7 | 0.9 |
| SD | 11.82 | 6.84 | 8.12 | 9.29 | 7.35 |

TABLE 3-continued

Vital Signs - Heart Rate (bpm)- Change from Test day Baseline

| Time Point | 20 µg (N = 45) | 125 µg (N = 43) | 250 µg (N = 41) | 400 µg (N = 40) | Placebo (N = 42) |
|---|---|---|---|---|---|
| Min | −20 | −15 | −24 | −27 | −16 |
| Median | 0.0 | −2.0 | −1.0 | −4.5 | 0.0 |
| Max | 50 | 19 | 20 | 12 | 16 |
| Change from pre-dose to 5 hours post-dose | | | | | |
| n | 45 | 40 | 40 | 39 | 41 |
| Mean | −0.0 | 1.2 | −1.4 | −3.1 | 1.6 |
| SD | 9.35 | 7.97 | 7.31 | 9.74 | 8.39 |
| Min | −20 | −13 | −22 | −23 | −18 |
| Median | 1.0 | 0.5 | 0.0 | −4.0 | 2.0 |
| Max | 19 | 22 | 13 | 22 | 19 |
| Change from pre-dose to 10 hours post-dose | | | | | |
| n | 43 | 39 | 39 | 38 | 39 |
| Mean | −3.4 | −2.1 | −3.6 | −6.4 | −2.1 |
| SD | 9.27 | 10.03 | 8.48 | 8.46 | 7.26 |
| Min | −26 | −21 | −26 | −26 | −18 |
| Median | −1.0 | −3.0 | −4.0 | −5.5 | −3.0 |
| Max | 11 | 37 | 17 | 10 | 12 |
| Change from pre-dose to 20 hours post-dose | | | | | |
| n | 44 | 40 | 39 | 36 | 40 |
| Mean | −3.6 | −2.5 | −3.4 | −5.6 | −2.4 |
| SD | 9.23 | 8.91 | 7.87 | 11.04 | 9.40 |
| Min | −29 | −25 | −22 | −29 | −20 |
| Median | −3.0 | −1.5 | −4.0 | −4.5 | −2.0 |
| Max | 17 | 23 | 12 | 18 | 23 |
| Change from pre-dose to 30 hours post-dose | | | | | |
| n | 43 | 38 | 38 | 36 | 39 |
| Mean | −2.7 | 2.8 | 1.0 | −1.4 | 0.3 |
| SD | 8.56 | 9.31 | 8.45 | 10.19 | 8.27 |
| Min | −24 | −18 | −21 | −29 | −20 |
| Median | −2.0 | 1.0 | 2.5 | 0.0 | 1.0 |
| Max | 13 | 28 | 19 | 16 | 11 |

TABLE 4

Vital Signs - Adjusted Means for Average Change in Heart Rate (bpm) from Test day Baseline to Scheduled Time-Point

| | Placebo | 20 µg | 125 µg | 250 µg | 400 µg |
|---|---|---|---|---|---|
| Change from Test day baseline to 45 mins post-dose | | | | | |
| n | 41 | 45 | 42 | 40 | 40 |
| Adjusted Mean | −2.328 | −2.323 | −2.854 | −3.693 | −7.052 |
| 95% CI | (−4.09422, −0.56267) | (−4.91033, 0.26356) | (−5.07662, −0.63184) | (−5.90752, −1.47803) | (−9.88041, −4.22321) |
| Dose v Placebo | | | | | |
| Difference | | 0.005 | −0.526 | −1.364 | −4.723 |
| 95% CI | | (−3.07363, 3.08375) | (−3.33005, 2.27848) | (−4.09076, 1.36209) | (−8.02112, −1.42561) |
| p-value | | 0.997 | 0.712 | 0.324 | 0.005 |
| Change from Test day baseline to 90 mins post-dose | | | | | |
| n | 41 | 45 | 42 | 39 | 40 |
| Adjusted Mean | 1.272 | 0.033 | −0.650 | −0.763 | −4.315 |
| 95% CI | (−0.74950, 3.29304) | (−2.92902, 2.99540) | (−3.20085, 1.90171) | (−3.32741, 1.80079) | (−7.55658, −1.07293) |

TABLE 4-continued

Vital Signs - Adjusted Means for Average Change in Heart Rate (bpm) from Test day Baseline to Scheduled Time-Point

|  | Placebo | 20 μg | 125 μg | 250 μg | 400 μg |
|---|---|---|---|---|---|
| Dose v Placebo | | | | | |
| Difference | | −1.239 | −1.921 | −2.035 | −5.587 |
| 95% CI | | (−4.76442, 2.28726) | (−5.13729, 1.29462) | (−5.17883, 1.10867) | (−9.36612, −1.80692) |
| p-value | | 0.489 | 0.240 | 0.203 | 0.004 |
| Change from Test day baseline to 5 hours post-dose | | | | | |
| n | 41 | 45 | 40 | 40 | 39 |
| Adjusted Mean | 2.047 | 1.933 | 2.382 | −0.586 | −3.455 |
| 95% CI | (0.19190, 3.90181) | (−0.79314, 4.65850) | (−0.02094, 4.78474) | (−2.91632, 1.74388) | (−6.43492, −0.47462) |
| Dose v Placebo | | | | | |
| Difference | | −0.114 | 0.335 | −2.633 | −5.502 |
| 95% CI | | (−3.35614, 3.12779) | (−2.66650, 3.33659) | (−5.49990, 0.23375) | (−8.97358, −2.02968) |
| p-value | | 0.945 | 0.826 | 0.072 | 0.002 |
| Change from Test day baseline to 10 hours post-dose | | | | | |
| n | 39 | 43 | 39 | 39 | 38 |
| Adjusted Mean | −1.824 | −0.126 | −0.186 | −4.657 | −6.919 |
| 95% CI | (−3.86270, 0.21448) | (−3.13166, 2.87986) | (−2.84168, 2.46964) | (−7.20022, −2.11286) | (−10.1839, −3.65480) |
| Dose v Placebo | | | | | |
| Difference | | 1.698 | 1.638 | −2.832 | −5.095 |
| 95% CI | | (−1.87535, 5.27177) | (−1.73715, 5.01331) | (−5.98176, 0.31690) | (−8.84274, −1.34775) |
| p-value | | 0.349 | 0.339 | 0.078 | 0.008 |
| Change from Test day baseline to 20 hours post-dose | | | | | |
| n | 40 | 44 | 40 | 39 | 36 |
| Adjusted Mean | −1.468 | −4.339 | −1.590 | −1.858 | −2.371 |
| 95% CI | (−3.20697, 0.27186) | (−6.94011, −1.73828) | (−3.83515, 0.65493) | (−4.05201, 0.33697) | (−5.20811, 0.46674) |
| Dose v Placebo | | | | | |
| Difference | | −2.872 | −0.123 | −0.390 | −0.903 |
| 95% CI | | (−5.95884, 0.21556) | (−2.96521, 2.72010) | (−3.05829, 2.27836) | (−4.15040, 2.34414) |
| p-value | | 0.068 | 0.932 | 0.773 | 0.583 |
| Change from Test day baseline to 30 hours post-dose | | | | | |
| n | 39 | 43 | 38 | 38 | 36 |
| Adjusted Mean | 0.619 | −0.880 | 2.796 | 1.436 | 0.475 |
| 95% CI | (−1.26084, 2.49824) | (−3.74493, 1.98437) | (0.29937, 5.29187) | (−0.93038, 3.80168) | (−2.55383, 3.50427) |
| Dose v Placebo | | | | | |
| Difference | | −1.499 | 2.177 | 0.817 | −0.143 |
| 95% CI | | (−4.85467, 1.85672) | (−0.92921, 5.28305) | (−2.09946, 3.73337) | (−3.62665, 3.33970) |
| p-value | | 0.379 | 0.168 | 0.581 | 0.935 |

Note:
Adjusted Means and CIs calculated using ANCOVA.

The invention claimed is:

1. A method of treating tachycardia, in a patient having tachycardia, by reducing the patient's heart rate for a period of at least 0.75 hours, said method comprising administering to the patient, via inhalation, an effective amount of an inhalable pharmaceutical composition comprising glycopyrrolate or a pharmaceutically acceptable salt thereof.

2. The method according to claim 1, wherein the composition is administered to a patient suffering from a respiratory condition selected from chronic obstructive pulmonary disease (COPD), asthma, cystic fibrosis (CF) and related airway diseases.

3. The method, according to claim 2, wherein the patient has COPD.

4. The method, according to claim 1, wherein the patient has tachycardia that has been pharmaceutically induced.

5. The method, according to claim 4, wherein the tachycardia has been induced by administration of salbutamol.

6. The method, according to claim 1, wherein the patient has tachycardia that is induced by an endocrine disorder.

7. The method, according to claim 1, wherein the patient has a form of tachycardia selected from the group consisting of ventricular tachycardia, supraventricular tachycardia, atrial fibrillation, AV nodal reentrant tachycardia (AVNRT), AV reentrant tachycardia (AVRT) and junctional tachycardia.

8. The method, according to claim 1, wherein the patient has a resting heart rate of greater than 90 beats per minute.

9. The method, according to claim 1, wherein the glycopyrrolate or a pharmaceutically acceptable salt thereof comprises glycopyrronium bromide.

10. The method, according to claim 1, wherein glycopyrrolate is present within the composition in an amount of between 10 and 500 µg.

11. The method, according to claim 10, wherein glycopyrrolate is present within the composition in an amount of 20 µg.

12. The method, according to claim 10, wherein glycopyrrolate is present within the composition in an amount of 400 µg.

13. The method according to claim 1, wherein the glycopyrrolate is administered once daily.

14. The method, according to claim 1, wherein the pharmaceutical composition is formulated as a dry powder formulation.

15. The method, according to claim 1, wherein the composition additionally comprises a force control agent.

16. The method, according to claim 15, wherein the force control agent comprises a metal stearate, or a derivative thereof.

17. The method, according to claim 16, wherein the force control agent comprises zinc stearate, magnesium stearate, calcium stearate, sodium stearate or lithium stearate.

18. The method, according to claim 17, wherein the force control agent comprises magnesium stearate.

19. The method, according to claim 1, wherein the composition further comprises lactose.

20. The method, according to claim 19, wherein the composition comprises 1% (w/w) glycopyrronium bromide and 99% (w/w) lactose.

21. The method, according to claim 19, wherein the composition comprises 1.05% (w/w) glycopyrronium bromide, 98.8% (w/w) lactose and 0.15% (w/w) magnesium stearate, or 1% (w/w) glycopyrronium bromide, 98.8% (w/w) lactose and 0.2% (w/w) magnesium stearate.

22. The method, according to claim 1, wherein the composition further comprises indacaterol.

23. The method, according to claim 1, wherein the composition further comprises a beta agonist.

24. The method, according to claim 1, wherein the patient is receiving concomitant treatment with a beta agonist.

25. The method according to claim 1, wherein the patient has been diagnosed with an increased heart rate.

* * * * *